United States Patent [19]

Connery et al.

[11] 4,076,596
[45] Feb. 28, 1978

[54] APPARATUS FOR ELECTROLYTICALLY DETERMINING A SPECIES IN A FLUID AND METHOD OF USE

[75] Inventors: James Gerard Connery, North Wales; Emil Christopher Muly, Doylestown; Robert Morgan Taylor, Lansdale, all of Pa.

[73] Assignee: Leeds & Northrup Company, North Wales, Pa.

[21] Appl. No.: 730,409

[22] Filed: Oct. 7, 1976

[51] Int. Cl.[2] ............................................. G01N 27/46
[52] U.S. Cl. .................................. 204/1 T; 204/195 P
[58] Field of Search ............... 204/195 P, 1 P, 1 B, 204/1 T, 195 R, 195 B; 128/2 E, 2.1 E; 324/29

[56] References Cited

U.S. PATENT DOCUMENTS

| | | | |
|---|---|---|---|
| 2,913,386 | 11/1959 | Clark | 204/195 P |
| 3,000,805 | 9/1961 | Carritt et al. | 204/195 P |
| 3,223,609 | 12/1965 | Reeds | 204/195 W |
| 3,240,693 | 3/1966 | Gardner | 204/195 W |
| 3,260,656 | 7/1966 | Ross | 204/1 T |
| 3,337,441 | 8/1967 | Goldsmith | 204/195 W |
| 3,474,022 | 10/1969 | Culpepper et al. | 204/195 R |
| 3,719,575 | 3/1973 | Niedrach et al. | 204/195 P |
| 3,763,850 | 10/1973 | Gaudebout et al. | 128/2 E |

FOREIGN PATENT DOCUMENTS

| | | | |
|---|---|---|---|
| 2,443,863 | 4/1975 | Germany | 324/29 |
| 704,552 | 2/1954 | United Kingdom | 204/195 R |

OTHER PUBLICATIONS

J. K. Fowler, et al., The Electrochemical Soc., pp. 290–311, (1975).

K. H. Mancy, In Situ Measurement of Dissolved Oxygen by Pulse & Steady State Voltammetric Membrane Electrode Systems.

*Primary Examiner*—G. L. Kaplan
*Attorney, Agent, or Firm*—William G. Miller, Jr.; Raymond F. MacKay

[57] ABSTRACT

An electrolytic cell for measuring the concentration of a species such as oxygen is constructed by depositing closely spaced interleaved inert electrode surfaces on the surface of an insulating substrate and covering the electrode surfaces with a thin film of electrolyte and permeable membrane. The electrolyte is selected so that the species being measured is generated at one electrode surface and consumed at the other with no net reaction in the electrolyte. Alternatively, a cylindrical configuration may be formed by closely winding two thin electrode wires about a cylindrical base and covering with an electrolyte and a membrane.

10 Claims, 7 Drawing Figures

APPARATUS FOR ELECTROLYTICALLY DETERMINING A SPECIES IN A FLUID AND METHOD OF USE

BACKGROUND OF THE INVENTION

This invention relates to electrochemical apparatus and more particularly to improved devices for electrically measuring the concentration of electrochemically active species in fluids.

The term "fluids" as used herein is intended to include gases, liquids, vapors and mixtures thereof. Heretofore, in the determination of the concentration in fluids of an electrochemically active species (a substance which is capable of being either reduced or oxidized at an electrode), electrochemical devices have been used in which an electrical characteristic of the species is measured and correlated with the concentration. Polarographic devices, for example, have been used measuring the diffusion-limited current at a characteristic potential at which such a species is electroreacted, such current being proportional to the species concentration. An improvement on the basic polarographic apparatus is the well known Clark cell described in U.S. Pat. No. 2,913,386 issued Nov. 17, 1959. The apparatus disclosed in that patent utilizes a dual electrode structure immersed in an electrolyte and encased at least in part in a membrane which is permeable to a predetermined species, for instance, gaseous oxygen. Typically, when used for oxygen analysis the cathode of a Clark apparatus is formed of platinum or gold and is located closely adjacent the membrane; the anode may be formed of silver in some cases and in some structures is made of lead and the electrolyte is usually an aqueous alkali halide solution. In operation such a device when used to measure oxygen has a membrane which is permeable to oxygen so that the oxygen in the fluid being tested, which is outside the membrane, permeates the membrane and is presumably reduced at the cathode to water in accordance with the overall equation

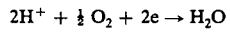

It will be apparent that the Clark cell is intended to reduce completely the oxygen permeating the membrane. The current ($2e$) necessary to effect this reduction is a measurement of the oxygen concentration in the test fluid. In determining oxygen concentration this device typically can employ the silver-silver chloride anode with a potassium chloride electrolyte solution. In that case the anode reaction would be

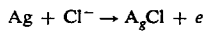

Where a lead electrode is used for the anode the reaction would be

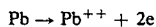

While devices of the type described above, normally referred to as Clark cells, have proved satisfactory for many purposes, several problems may be encountered in certain applications. Some of the disadvantages which are inherent in the Clark type cell arises from the fact that the reactions which give rise to the measured current irreversibly change the internal solution composition. This change may in some cases alter the pH of the electrolyte in time, and result in the physical consumption of the anode. Thus, there may be required either a means for maintaining the pH of the electrolyte as by use of a buffer and/or the supply of sufficient electrode material and electrolyte to withstand the changes without significantly altering the system properties.

Certain of the other problems encountered with the Clark system are more readily understood by reference to FIG. 1, a graphic presentation of the concentration diagram for such devices. In this diagram, the ordinate 60 is the scale from zero of the relative fugacity of oxygen, and the abscissa represents the distance from the cathode-membrane interface toward a test fluid. The position of the cathode-membrane interface (neglecting any small displacement between the two), is at line 60. Line 62, parallel to the ordinate, then represents the membrane-test fluid interface. The distance between lines 60 and 62 is representative of the membrane thickness. Now it may be assumed that the concentration of oxygen in the test fluid adjacent to the outer surface of the membrane is constant, as shown by the horizontal portion of the broken line 64, and that the consumption of oxygen at the cathode is complete so that the concentration of oxygen at the cathode-membrane interface is substantially zero. Under such circumstances the concentration gradient, represented by the remainder of broken line 64, across the membrane is approximately linear and its slope is an inverse function of the membrane thickness.

However, during actual operation of the device, as oxygen is consumed at the cathode, there is a continual flow of the gas from the test fluid through the membrane to replenish the oxygen supply being consumed or reduced. If the oxygen in the test fluid adjacent to the outer surface of the membrane is not continually replenished so as to be maintained at a constant level, the concentration gradient will then extend out into the test fluid, and its slope will become non-linear and reduced as shown at broken line 66 in FIG. 1, due to the local depletion of oxygen in a layer shown between lines 62 and 68. With continued operation of the device and no replenishment of oxygen, the local depletion layer will continue to expand further out into the test fluid, distorting the concentration gradient more and more. The distortion of the concentration gradient reduces the measurement sensitivity and change the mass flow rate of oxygen through the membrane to the cathode, making measurement uncertain and even spurious over a period of time. In order to avoid such occurrence, several means are customarily provided to minimize the extension of the depletion layer into the sample. A minimum fluid flow past the membrane-fluid interface is established, as for instance by stirring, and/or a relatively low permeability membrane may be used perhaps in combination with an inert spacer positioned between the cathode and the membrane thereby increasing the thickness of the electrolyte layer, lessening the flux of the consumed species and minimizing the establishment of the depletion layer in the test fluid.

Further, if the fluid under measurement is a minute sample to which access is restricted, as is frequently the case with clinical samples of biological fluids or cells, depletion will continue until all of the oxygen is consumed. If the consumed oxygen is not or cannot be readily renewed, the measurements in a short time become inconclusive. The input flow rate of the oxygen is often controlled by providing a relatively thick membrane which, however, acts to slow the response time of the device to changes in the oxygen concentration in the test fluid and lessens the magnitude of the signal current.

Further, it is common for the outer surface of the membrane, at line 62, to become fouled to some extent while in use. This problem is particularly acute in applications where the sample is heavily laden with algae, bacterial growth, or particulate. The additional impedance to oxygen flux presented by the fouling causes a diminution of the sensor signal and renders the measurement inconclusive. Wipers to clean the interface, in combination with frequent replacement of the membranes, have been used to minimize this problem.

Some of the above mentioned disadvantages of the Clark type electrode cell are avoided by apparatus of the type described in U.S. Pat. No. 3,260,656 issued to James W. Ross, Jr. on July 12, 1966. The Ross apparatus utilizes a sandwich comprising a cathode and an anode with a spacer between. This sandwich is immersed in an electrolyte and is geometrically oriented so that the electrodes are parallel to a membrane which is permeable to the species being measured. The membrane combines with a housing to enclose the cathode-anode combination in an electrolyte. Typically, as for example, for the measurement of oxygen concentration, the Ross electrode cell utilizes an anode which is formed of a sheet-like element typically having a thickness of about three mils and being porous to both the electrolyte and the electroactive species being measured. The anode is made of an electrically conductive material, preferably a noble metal such as platinum, gold or the like. To provide porosity the anode may be provided as a mesh or screen. The cathode, on the other hand, can be formed of substantially sheet-like material and may be solid and has a thickness which need be determined only by cost and structural strength considerations. The cathode is also preferably made of a noble metal and may be the same metal as the anode. The cathode-anode sandwich is disposed in an electrolyte which is preferably an aqueous solution of a base such as KOH. The spacer between the anode and cathode may, for example, be a sheet-like porous element such as a woven fabric which is electrically non-conductive and chemically inert to the electrolyte.

With the Ross cell, if a potential is applied across the anode and cathode that is well below the decomposition voltage of the electrolyte and if there is no oxygen available in the electrolyte (as from diffusion into the electrolyte through the membrane or from being dissolved in the latter), only a virtually constant, minute, residual current will flow in the cathode-anode circuit. If, however, a supply of oxygen is presented to the outer surface of the membrane, as by contacting the membrane with a liquid having a dissolved oxygen content, or by contacting it with a gas which includes oxygen, then because of the selective permeability of the membrane some oxygen will diffuse through the membrane and thence into the electrolyte to the cathode. If the potential at the cathode is more negative than the reduction potential of oxygen although below the decomposition potential of the electrolyte, oxygen present at the cathode will be reduced. The reduction process is believed to be according to the same equation applicable to the cathodic reduction in the Clark apparatus. With the choice of electrode elements as mentioned above, the anode will cause, by virtue of the anode current, an oxidizing of the water in the electrolyte to generate oxygen according to the following $$H_2O \rightarrow \tfrac{1}{2} O_2 + 2H^+ + 2e$$

while at the cathode the oxygen reduction occurring is believed to be described by the same equation heretofore used to describe the cathode reduction in the Clark apparatus.

It will then be obvious that the system consumes the species being measured at one electrode such as the cathode and tends to generate a like quantity of that species at the opposite polarity electrode such as the anode, without changing the system such as changing the electrolyte pH and with an appropriate selection of electrode material consumption of the electrode can be avoided and the electrolyte will remain unchanged. The steady-state equality between generation and consumption of oxygen is, however, responsive to any change in concentration of the oxygen outside of the membrane. The gas tensions on both sides of the membrane will tend to reach an equilibrium with one another, thus any change in gas tension outside the membrane will upset the internal steady-state activity of the electrode system forcing it to a new steady-state by either increasing or decreasing the consumption of gas at one electrode with a corresponding increase or decrease in the generation of gas at the other electrode. Each change in gas generation is thus in a direction tending to establish equilibrium between the gas tensions on opposite sides of the membrane and each change in the internal steady-state is accompanied by a change in current flow between the electrodes so that the current flow is generally maintained in direct proportion to the concentration of the oxygen gas, for example, outside the membrane.

Referring to FIG. 2, there is shown graphically a concentration diagram taken across the electrode-membrane structure of the Ross apparatus. As in FIG. 1, the ordinate 70 represents the relative fugacity of the particular electroactive species. The absicissa 72 represents distance from the cathode-electrolyte interface which is at the origin of the graph and hence, in a sense, the latter interface is line 70. Lines 74 and 76 then represent surfaces of an anode positioned between the cathode and membrane, with line 74 representing the surface facing the cathode and line 76 the membrane. Line 78 is the outer surface of the membrane in contact with the test fluid. For the sake of clarity, no displacement between anode and membrane is shown, hence line 76 can also be considered the anode-membrane interface. The displacement between the anode and cathode in the Ross apparatus is maintained by the spacer screen defining the electrolyte layer thickness between lines 70 and 74.

Given the geometry of the Ross apparatus, wherein the generating electrode lies between the consuming electrode and the test fluid, and assuming that the oxygen exhibits the same tension in both the electrolyte and test fluid and the concentration of oxygen in the test fluid is constant, the latter concentration is indicated by the horizontal portion of the broken line 80 which extends from the test fluid into the membrane. The concentration gradient, represented by the remainder of broken line 80, extends presumably from the anode-membrane interface to the cathode-electrolyte interface.

Whereas the Ross cell effectively overcomes the problems of alteration of the electrodes and/or electrolyte, depletion of the oxygen from the test fluid, and extension of the depletion layer into the test fluid causing stirring and fouling dependence, certain other shortcomings are still evident. Among them is the fact that readings with the Ross type cell, obtained by measuring the current flow between the electrodes, tend to stabilize within a maximum of one minute in accordance with the Ross patent. It has been found that response times of this order for continuous measurements, such as the continuous measurement of oxygen concentration, are not suitable for many applications. Increasing the speed of response of the Ross type cell would require decreasing the combined thickness of the electrolyte layer (i.e. the spacer screen thickness) and of the generating electrode, which are already at or near the practical minimum size for these components.

A further disadvantage is the fact that the diffusion layer thickness in the Ross cell is determined by the interelectrode distance, which is subject to variation as the assembly is stressed by forces arising from temperature and/or pressure variations. Not only may the spacing vary, it cannot be less than a few mils to accommodate the spacer screen. Whereas the thickness of the diffusion layer is inversely related to the signal magnitude, an extremely thin and stable diffusion layer is preferred.

A further disadvantage is the cumbersome nature of the layered structure, making reliable fabrication of Ross type devices difficult.

The Ross approach is not the only attempt to overcome the recognized deficiencies of the Clark electrode. Among others, K. H. Mancy used a pulse polarographic technique and J. K. Fowler and K. B. Oldhen used semi-integral amperometry (both reported in "Chemistry and Physics of Aqueous Gas Solutions", The Electrochemical Society, 1975) to minimize Clark electrode shortcomings. However both did so at the expense of complex electronics and at the sacrifice of speed of response, which could exceed one minute.

It is therefore an object of this invention to provide an improved electrode structure which will have all of the advantages of the Clark cell and the improvements of the Ross cell while overcoming their disadvantages. Accordingly, the present invention contemplates an improved electrolytic cell for measuring species concentration in a fluid with increased sensitivity, greater stability and shorter response time when compared to prior art devices such as the Ross cell.

SUMMARY OF THE INVENTION

There is provided a voltammetric cell for measuring the concentration of electrochemically active species in a fluid which comprises an electrolytic medium from which only the species is electrolytically generable. Barrier means such as a membrane may be provided where necessary for separating the electrolytic medium from the fluid whose concentration is to be measured. That barrier means is permeable to the species. The cell also includes a plurality of spaced electrode surfaces arranged for connection to a power source so as to provide adjacent electrode surfaces with alternate polarities. The surfaces are positioned so as to define a surface which is everywhere equidistant from and in close spaced relationship to the barrier means with the electrolytic medium interposed therebetween and the electrode spacing and electrode surface width determining a periodicity of electrode positioning sufficiently small with respect to the thickness and to the species permeability of both the barrier and the electrolyte so that as the species is generated at surfaces of one polarity the species is consumed at the surfaces of opposite polarity in quantity dependent upon the concentration of the species in the fluid being measured so that there is negligible flux of the species across the interface between the barrier and the fluid.

DESCRIPTION OF THE PREFERRED EMBODIMENTS

Figure 3:
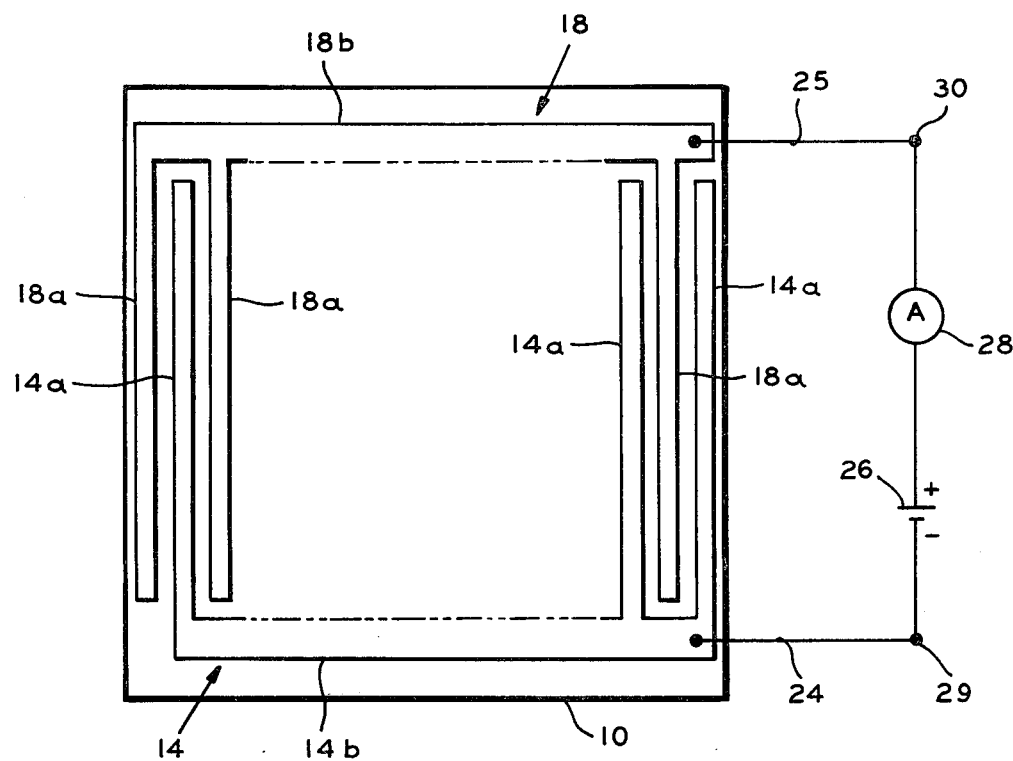
FIG. 3 is an elevated view of a portion of the cell of the present invention including the electrode surfaces.

In FIG. 3 there is shown a portion of the electrolytic cell which consists of a non-conductive substrate 10 upon which there is deposited both anodic and cathodic electrode surfaces, preferably in the form of a thin metal film. For example, the cathode 14 is shown as having finger-like projections 14a projecting from the main body 14b. Those finger-like projections are interleaved with the finger-like projections 18a projecting from the main body 18b of the anode 18. The cathode and anode are interconnected in operation by an electrical circuit through leads 24 and 25 to an electrical circuit connected to the respective terminals 29 and 30. That electrical circuit contains a series connected potential source 26 and an ammeter 28.

Figure 4:
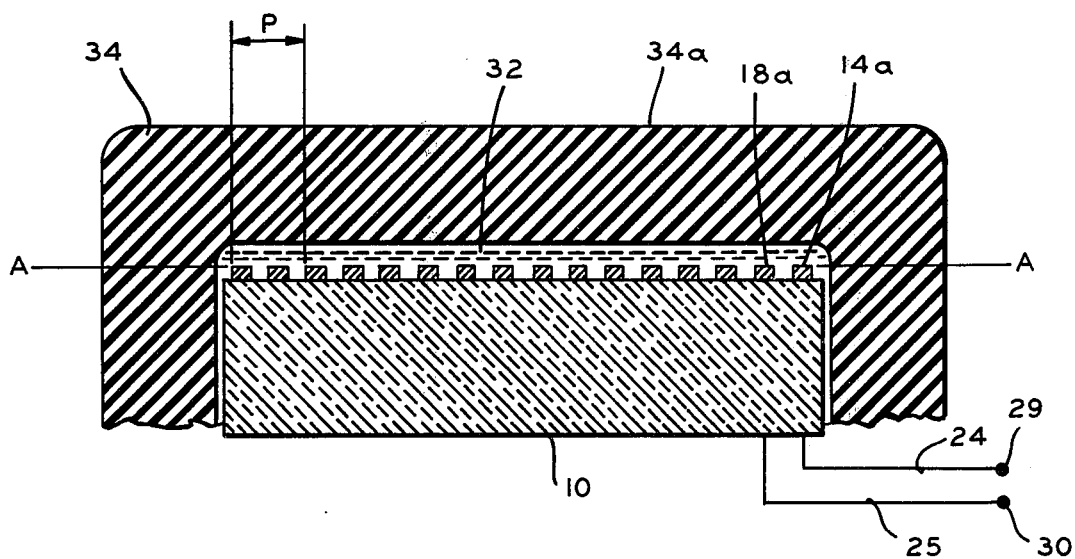
FIG. 4 is a cross-section view of the cell.

The structure of the electrolytic cell in one form is more completely shown in cross-section in FIG. 4 where the substrate 10 is shown as having its cathode as formed by the finger-like projections 14a connected by way of line 24 to terminal 29 and the projections 18a forming the anode connected by line 25 to terminal 30. The main portions 14b and 18b of the cathode and anode may preferably be insulated from the circuit formed by the anode and cathode elements 14a and 18a by any of a number of means such as by covering the respective main body portion with insulating material.

The anode and cathode surfaces are in contact with an electrolytic medium 32 which may advantageously consist of a thin film of liquid electrolyte distributed over the electrode surfaces. That electrolyte may be contained at the electrode surfaces by the barrier means 34 which is a membrane permeable to the species whose concentration is to be measured by the cell.

If, for example, the cell shown in FIGS. 3 and 4 is to be used for the measurement of the concentration of oxygen in a fluid, the fluid is maintained in contact with the membrane 34 which can advantageously be constructed of silicone rubber material, for example. The electrolyte 32 confined to contact with the surfaces of the electrode elements 14a and 18a may advantageously be KOH while the electrode material for the cathode 14a may be silver and the anode material for the anode 18a may be platinum. It will, of course, be understood that other noble metals may be used, however, the relative chemical inertness of the silver cathode and the platinum anode material has been found advantageously for the oxygen measurement. The substrate 10 may be of many suitable insulating materials such as glass, quartz, ceramics such as alumina, etc., having a thickness of greater than 10 mils, or sufficient to assure structural integrity.

The substrate 10 may advantageously be mounted on a supporting body over which the membrane 34 may be fitted and to which the membrane 34 may be affixed as by the use of cement or by being held in place by an "O" ring, for example. The method of mounting the substrate 10 and the method of fixing and retaining the membrane 34 in place can, of course, be selectively chosen depending upon the application for which the cell is to be used. It will, of course, be understood that the cell structure of FIGS. 3 and 4 may be suitable for the detection of species other than oxygen in which case appropriate barrier 34 may be selected so that it is permeable to the species being measured and the material from which the anode and cathode are made may be appropriately selected so that when used in conjunction with a selected electrolytic medium the particular species to be measured is generated at the surface of the electrode of one polarity while it is consumed at the surface of the electrode of the opposite polarity in a quantity which will be dependent on the concentration of the species in the fluid to be measured and so that there is a negligible transfer of the species across the interface between the membrane barrier and the fluid as, for example, the surface 34a of the barrier 34. Operation of the cell in avoidance of any substantial transfer of species across interface 34a will depend upon the relative dimensions of the elements of the cell, that is, the spacing between the electrodes 14a and 18a and the thickness of the electrolytic medium in combination with the thickness of the barrier means. Those dimensions will be such that the flux of the species transferred between anode and cathode will be substantially all within the electrolytic medium and the barrier means.

As mentioned, the choice of electrolyte 32 will depend, of course, upon the species to be measured, it being necessary that the electrolytic medium formed by the electrolyte should be such that only the species to be measured is electrolytically generable therefrom.

The spacing of the electrode surfaces and the width of those surfaces in their side-by-side configuration, as shown in FIGS. 3 and 4, should, to fulfill the requirements of minimum transfer of species across interface 34a, be such that the periodicity of the electrode positioning established by the period P between corresponding portions of adjacent electrode surfaces of the same polarity is sufficiently small with respect to the thickness and species permeability of both the barrier 34 and the electrolytic medium 32 so that as the species generated at the electrode surface of one polarity is consumed at the surface of the opposite polarity with only an insignificantly small fraction transferring therebetween by crossing surface 34a. Thus the electrolyte is subjected to no net chemical reaction. The reactions involved for the oxygen measuring cell may, for example, be the same as those set forth for the Ross cell.

It will, of course, be evident that the concentration of other electrochemically active species may be determined as, for example, chlorine which can be determined using the oxidation reduction reaction

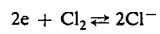

It will thus be evident that in an operation of the cell as, for example, in the measurement of the concentration of the oxygen in the sample being measured, the oxygen from the sample diffuses through the membrane 34 to bring the system to compositional equilibrium. Thus, the oxygen tension in the sample being measured will equilibrate with the average oxygen tension in the electrolyte 32. All of the oxygen reaching the surface of the cathode is consumed while a like amount of oxygen is generated simultaneously at the anode. There then results an oxygen flux from the anodes to the adjacent cathodes; however, since not net change in oxygen content results substantially no oxygen flux crosses the membrane interface 34a unless the sample composition changes. This absence of flux crossing the membrane interface 34a occurs providing, as mentioned, that the periodicity of the electrode surface spacing P is sufficiently small with respect to the combined thickness of the barrier membrane 34 and electrolyte 32 and the species permeability of both the barrier and the electrolyte are such that substantially all of the oxygen flux is confined within the electrolyte and membrane.

Figure 1:
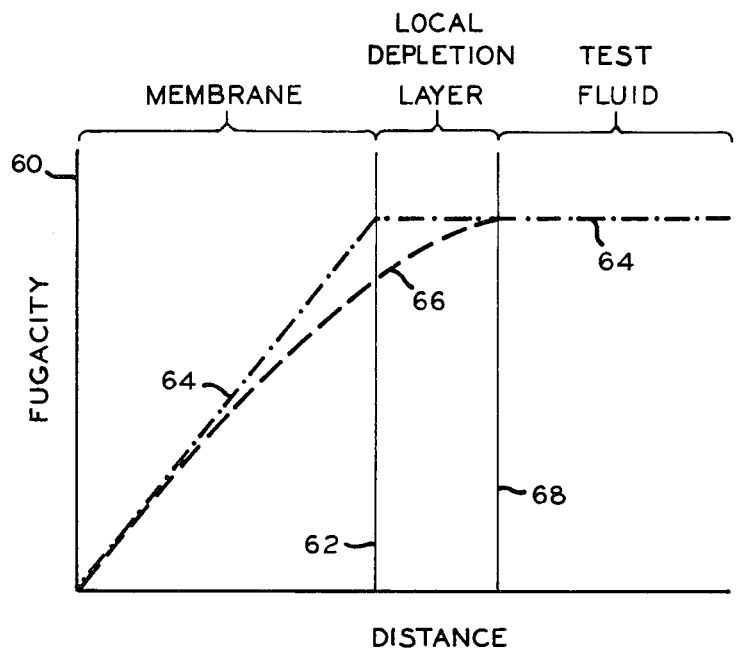
FIG. 1 is a graphical representation of the concentration gradient across the selectively permeable membrane in Clark type prior art devices as hereinbefore described.
Figure 2:
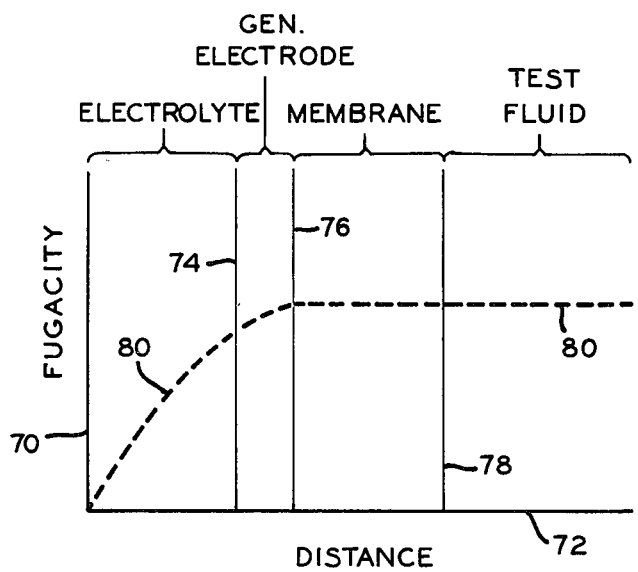
FIG. 2 is a graphical representation of the concentration gradient through the electrolyte-electrode structure of Ross type prior art devices as hereinbefore described.
Figure 5:
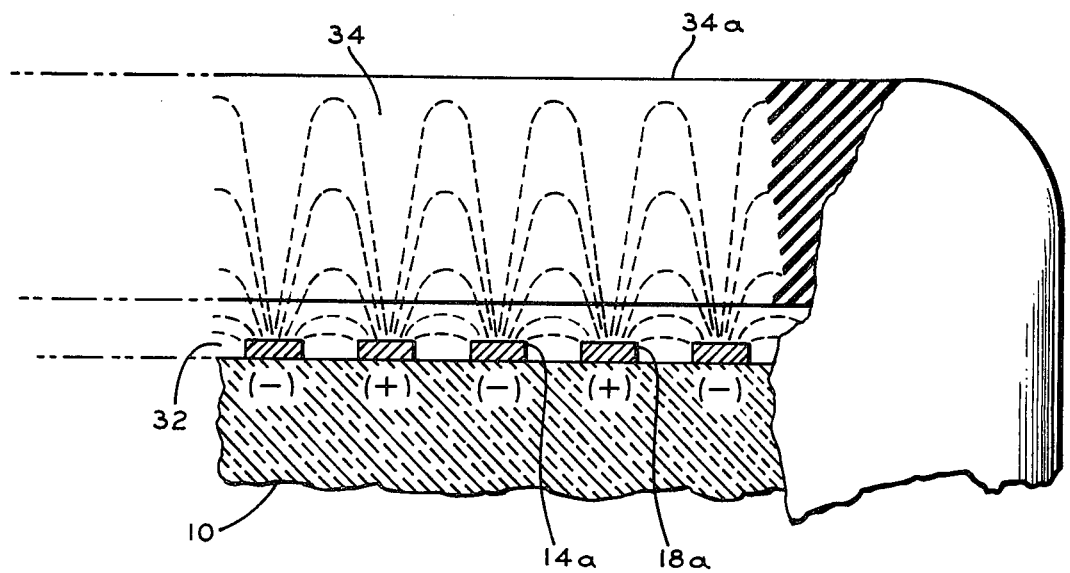
FIG. 5 is a graphical representation of the flux paths through the permeable membrane.

It is not possible to show a graphical representation of the concentration gradient across the selective membrane or through the electrolyte of the present invention as was done in FIGS. 1 and 2 for prior art devices. This is the case because the concentration of oxygen, for example, varies not only with the distance from the electrode-electrolyte interface but also periodically across planes parallel to the plane of the electrode surfaces with the periodicity of the electrode structure. FIG. 5 shows graphically the flux patterns occurring during operation of this invention as dotted lines superimposed on a cross-section view of the device. Oxygen is generated at the anodes 18a which are on inert substrate 10, and diffuses to the cathodes 14a, some transversing the intermediate space via the electrolyte 32 and some through the permeable membrane 34. With proper choice of membrane material and the membrane thickness/electrode period ratio, only an insignificant quantity of oxygen will diffuse across interface 34a between the membrane and the test fluid.

With the geometrical configuration of the electrode surfaces, as shown in FIG. 4, the spaced electrode surfaces are arranged for connection so that adjacent electrode surfaces have alternate polarities and so that those surfaces define a surface A—A which is everywhere equidistant from and in close space relationship to the barrier means comprising membrane 34 with the electrolyte medium 32 interposed therebetween.

With the above structure the deficiencies of the Clark cell as well as the Ross cell can be minimized or eliminated. This is the case since there is no net reaction in the cell with the exception of the consumption of a small amount of electrical power so that there is no reagent consumption or product build-up and no depletion of the oxygen in the sample.

Since there is substantially no oxygen flux through the outer surface of the membrane except during periods of transient change in the sample there will not be a concentration gradient into the solution and therefore no minimum flow past the cell is required. The lack of oxygen flux through the outer surface of the membrane also removes the problem of the temperature coefficient for oxygen flux passing completely through the membrane no longer plays a roll in the cell's response other than in influencing response time. Thus, the signal produced by the cell varies with temperature as does the diffusion coefficient of the species being measured. With oxygen in aqueous solution variations would be two or three percent per degree.

Other advantages to the present invention as compared with the Clark and Ross cells include the fact that fouling of the membrane surface will not affect the calibration curve of the cell since there is no oxygen flux completely through the membrane during steady-state operation whereas, as pointed out, the Clark cell typically suffers from continual signal loss as fouling builds up. Thus, the calibration of the cell of the present invention remains unchanged. In addition, the diffusion layer thickness is decreased by having the oxygen generated at an electrode surface in close proximity to the surface where it is depleted. For a given electrode area the oxygen concentration is higher for the structure of this invention than for the Clark or Ross cells. Therefore, an improvement in the sensitivity of the cell is inherent in the novel structure of the cell as described and an improvement in signal level of a factor in the order of 10 to 100 has been observed in oxygen measurements where the periodicity of the spacing of the electrode surfaces is on the order of 1.6 mils with a membrane thickness of 5 mils.

The manner of construction, which may advantageously be utilized for the cell of FIGS. 3 and 4, can be any one of a number of techniques including thick and thin film techniques, however, it is believed that the thin film construction techniques which may, for example, involve the sputtering and/or evaporation onto the substrate surface of a thin film of metal to form the electrode surfaces with the definition of the surface areas being accomplished by photo-etching processes is a preferred construction technique.

The electrolyte solution itself may, as mentioned, be nothing more than a film of electrolyte over the electrode surfaces and the electrolyte solutions may be any of a number of alternatives including hydroxides, carbonates, sulfates, or combinations thereof. With the structure set forth in FIGS. 3 and 4 the present invention provides a fast responding sensitive measurement in comparison with the prior art systems for in addition to overcoming the disadvantages of the Clark and Ross cells, as pointed out above, the present invention provides a cell which not only has a faster response time and an increased sensitivity but also a symmetrical response and an avoidance of out-gassing at the anode which can occur, for example, with the Ross cell under certain conditions.

Figure 6:
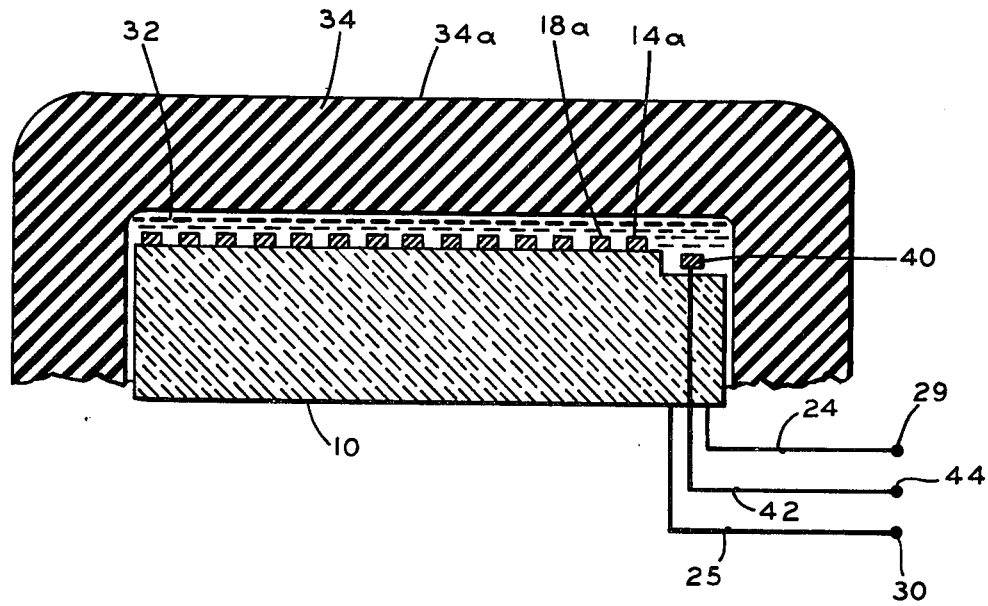
FIG. 6 is a cross-section view of a cell similar to FIG. 4 but with the inclusion of a third electrode.

In FIG. 6, there is shown a variation of the cell shown in FIGS. 3 and 4 in that the cell of FIG. 6 includes, in addition to the cathode and anode surfaces 14a and 18a, respectively, a reference electrode 40 which is connected by way of line 42 to terminal 44.

The cell of FIG. 6 may utilize a measuring circuit of the type shown in FIG. 6 of the Ross patent for measuring species concentration. While the anode and cathode surfaces of the present invention have been shown in FIGS. 3, 4, and 6 in a form whereby the electrode surfaces define a flat plane A—A, the cell may be arranged so that the electrode surfaces define a cylindrical plane, for example, as in the arrangement of FIG. 7 where the membrane 46 is shown as being in a tubular form overlaying the cell electrodes and their support which consists of a central cylindrical body 48 of insulating material which has wound on its surface two interleaved wire electrodes forming spirals about the central support 48. These electrodes may consist of a wire 50 which forms an anode for the cell and the wire 52 which forms a cathode. In order to appropriately expose electrode surfaces to the electrolyte 54 which is interposed between the membrane 46 and the electrodes 50 and 52, the cell of FIG. 7 may be constructed by winding upon the cylindrical base 48 the wires 50 and 52 and then immersing the resulting structure in a potting compound such as epoxy, for example, so that the assembly is completely potted. Then the potted assembly can be turned down on a lathe until sufficient amount of potting compounds is removed to expose a small surface area of the wires 50 and 52 to form along the length of the cylindrical electrode assembly interleaved cathodic and anodic surfaces.

The spacing between the wires 50 and 52 and the width of the exposed surfaces should be such that the appropriate periodicity of the electrode surface is provided and, as mentioned with regard to the structures of FIGS. 3 and 4, that periodicity should be small with respect to the thickness and the species permeability of both the barrier and the electrolyte so that as the species is generated at the surface of one electrode it is consumed at the surface of the other electrode in a quantity dependent on the concentration of the species in the sample fluid being measured with negligible transfer of the species across interface between the barrier membrane 46 and the sample being measured.

Figure 7:
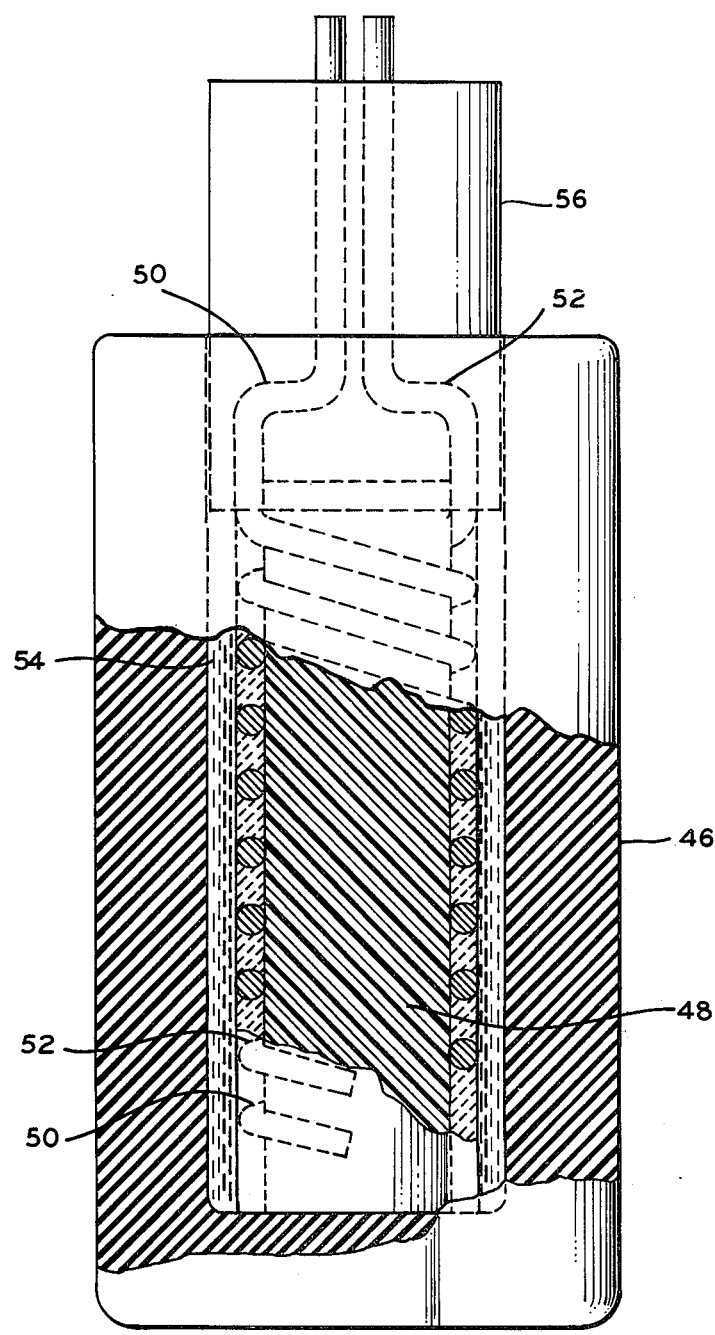
FIG. 7 is a cross-section view of another form of cell showing the use of two electrodes.

The cylindrical electrode inserted in the membrane 46, as shown in FIG. 7, is supported by a non-conducting body portion 56 to which the membrane 46 is closely fitted so as to retain the electrolyte 54 within the spacing between the membrane 46 and the inserted electrode structure carrying the electrode surfaces on wires 50 and 52. As with the structure of the other configurations the electrolyte need consist only of a thin film of electrolyte solution in order to maximize the sensitivity and minimize the response time of the electrode.

The electrolyte 32 of FIGS. 4, 5 and 6 as well as the electrolyte 54 of FIG. 7 can be a solid polymer electrolyte instead of being a liquid electrolyte as mentioned. The polymer electrolyte must allow diffusion of all reactants and products between the cathodes and anodes as well as allowing exchange of the measured gas with the test fluid. It must also have satisfactory chemical, thermal and dimensional stability. Such polymer electrolytes may be poly-sulfonic acids, typically polystyrene sulfonic acid or perfluoro linear polymers (such as marketed under the name "Nafion" by Du Pont).

The barrier 34 of FIGS. 4, 5 and 6 and the barrier 46 of FIG. 7 may be omitted when there is no necessity to isolate the test fluid from the electrolyte. For example, when the test fluid is a gas, such isolation is not necessary. This is particularly true when the electrolyte is a solid.

The following example is illustrative of the construction and operation of a device shown in FIG. 7. A non-conducting body 1.587 cm in diameter was formed of polyformaldehyde such as Delrin marketed by Du Pont. Silver wire 0.006 inch in diameter was used for the cathode and 0.006 inch diameter platinum wire for the anode. Forty turns of the wires were wound in a bifilar configuration around the cylinder, the wires spaced 0.006 inches apart. The assembly was then potted in an epoxy and, after curing, the epoxy surface was removed to expose the wire surfaces. A thin layer of 0.1M NaOH was held against the electrode surfaces by a 0.005 inch thick silicone rubber membrane. The assembly was immersed in an aqueous solution which was alternately purged with air or nitrogen. During nitrogen purge a signal of 0.08 ma was obtained, whereas in air purged solution the signal was 1.73 ma. The response time was 5 seconds for 90% response and approximately 8 seconds for the full change in output.

The following example is illustrative of the construction and operation of a device shown in FIGS. 3 and 4. A non-conductive glass substrate 0.5 inch square and 0.02 inch thick was used, onto which was sputtered 200 platinum electrode surfaces 10 micron wide and 4 mm long separated by 10 micron spaces. Connection was made such that there were 100 cathodes alternating with 100 anodes. Bus bars and lead wires were isolated from contact with the electrolyte by an epoxy film coating. An extract of a solid cation electrolyte such as that previously identified as Nafion was deposited as a thin film on the electrode pattern and covered with a thin layer of silicone rubber. When immersed in an $N_2$ purged aqueous solution, the output current was 0.1 microamperes. In air saturated solution, vigorously stirred, the signal was 12.4 microamperes, which decayed to 11.8 microamperes when the solution was left with no stirring for over one hour. A Clark type device operated in like manner lost over 70% of its signal when left unstirred.

It will be apparent to those skilled in the art that many modifications of the invention as thus described can be made. For example, a large number of electrolytes may be used. Indeed, under some circumstances the electrolyte may be a molten salt, and the enclosure means a membrane selected accordingly to have appropriate temperature resistant characteristics. It will also be apparent that where the species to be measured is reducible, the generating electrode is an anode and the consuming electrode is a cathode. However if the species to be measured is oxidizable, the generating electrode will be a negative electrode and the consuming electrode will be an anode or positive electrode.

What is claimed is:

1. In an electrode assembly for measuring the concentration of oxygen in a fluid of the type which includes in combination:
   an electrolytic medium;
   first electrode means having surfaces in contact with said medium;
   barrier means for separating said medium from said fluid, and being selectively permeable to said oxygen, and in contact with said medium;
   an electrical power source connected for biasing said first electrode means at a potential at which said oxygen in said medium will be consumed at said surfaces of said first electrode means; and
   second electrode means having surfaces in contact with said medium and connected to said power source for completing a circuit in which a current from said source can flow through both said electrode means at a level which is a function of such consumption;
   said second electrode means and said medium being such that with the combination substantially only said oxygen is electrolytically generable at said second electrode means at said current level, said second electrode means being biased by said power source at a potential at which said oxygen is generable from said medium; the improvement comprising,
   the positioning of said second electrode means with respect to said first electrode means so that said surfaces of said first electrode means are interleaved in side by side relationship with said surfaces of said second electrode means with said surfaces of said electrodes equidistant from said barrier means and the periodicity of said positioning sufficiently small with respect to the thickness and permeability of both said barrier means and said medium to oxygen so that the oxygen generated at said second electrode is consumed at said first electrode without any substantial transfer of oxygen across the interface between said barrier means and said fluids.

2. An electrode assembly as set forth in claim 1 in which said surfaces of said first and second electrode means define a surface which is a flat plane.

3. An electrode assembly as set forth in claim 2 in which said surface of said first and second electrode means are formed by a plurality of thin metal film strips deposited on an insulating flat substrate so as to be closely spaced.

4. An electrode assembly as set forth in claim 1 in which said surfaces of said first and second electrode means define a surface which is cylindrical.

5. An electrode assembly as set forth in claim 1 in which said electrolytic medium is a thin film of liquid electrolyte.

6. An electrode assembly as set forth in claim 1 in which said electrolytic medium is a thin film of solid electrolyte.

7. An electrode assembly as set forth in claim 1 which includes a reference electrode contacting said medium and spaced from said first and second electrode means.

8. An electrode assembly as set forth in claim 1 in which
   said electrolytic medium is a solid polymer electrolyte; and
   said first and second electrode means are formed by narrow strips of thin metal film deposited on a flat insulating substrate.

9. In an electrode assembly for measuring the concentration of chlorine in a fluid of the type which includes in combination:
   an electrolytic medium;
   first electrode means having surfaces in contact with said medium;
   barrier means for separating said medium from said fluid, and being selectively permeable to said chlorine, and in contact with said medium;
   an electrical power source connected for biasing said first electrode means at a potential at which said chlorine in said medium will be consumed at said surfaces of said first electrode means; and
   second electrode means having surfaces in contact with said medium and connected to said power source for completing a circuit in which a current from said source can flow through both said electrode means at a level which is a function of such consumption;
   said second electrode means and said medium being such that with the combination substantially only said chlorine is electrolytically generable at said second electrode means at said current level, said second electrode means being biased by said power source at a potential at which said chlorine is generable from said medium; the improvement comprising, The positioning of said second electrode means with respect to said first electrode means so that said surfaces of said first electrode means are interleaved in side by side relationship with said surfaces of said second electrode means with said surfaces of said electrodes equidistant from said barrier means and the periodicity of said positioning sufficiently small with respect to the thickness and permeability of both said barrier means and said medium to chlorine so that the chlorine generated at said second electrode is consumed at said first electrode without any substantial transfer of chlorine across the interface between said barrier means and said fluid.

10. The method of measuring the concentration of an electrochemically active species in a fluid comprising the steps of:

immersing in said fluid an electrode assembly including:

an electrolytic medium from which only said species is electrolytically generable, barrier means selectively permeable to said species, first electrode means of material electro-chemically inert to both said medium and said species and having surfaces in contact with said medium, second electrode means of material electro-chemically inert to both said medium and said species, said second electrode means having surfaces in contact with said medium, means for supporting said first and second electrode means to position their respective surfaces in contact with said medium in an interleaved side by side relationship with said surfaces equidistant from said barrier means and positioned so that the periodicity of the spacing of said electrode surfaces is sufficiently small with respect to the thickness and species permeability of both said barrier means and said medium so that the species generated at the surfaces of said second electrode is consumed at the adjacent surfaces of said first electrode without any substantial transfer of said species across the interface between said barrier means and said fluid, and means connecting said first and second electrodes to a power source operable to bias said first and second electrodes at potentials to produce a current between said electrodes such that said species will be generated at said second electrode and consumed at said first electrode in quantity dependent upon the tendency of said species to establish an equilibrium condition across said barrier means between the respective concentrations of said species in said medium and said fluid; and measuring said current flow as an indication of said species concentration in said fluid.

* * * * *